(12) United States Patent
Rope et al.

(10) Patent No.: US 9,299,173 B2
(45) Date of Patent: Mar. 29, 2016

(54) AUTOMATIC SELECTION OF DIFFERENT VISUALIZATIONS FOR THE ORGANIZATION OF MULTIVARIATE DATA

(75) Inventors: Daniel J. Rope, Reston, VA (US); Graham J. Wills, Naperville, IL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 13/154,594

(22) Filed: Jun. 7, 2011

(65) Prior Publication Data

US 2012/0313947 A1    Dec. 13, 2012

(51) Int. Cl.
*G06T 11/20* (2006.01)
*G06F 17/30* (2006.01)
*G06F 17/24* (2006.01)
*G06F 19/00* (2011.01)

(52) U.S. Cl.
CPC ............ *G06T 11/206* (2013.01); *G06F 17/246* (2013.01); *G06F 17/30572* (2013.01); *G06F 17/30991* (2013.01); *G06F 19/3487* (2013.01)

(58) Field of Classification Search
USPC ......................................................... 345/440
See application file for complete search history.

(56) References Cited

U.S. PATENT DOCUMENTS

| | | | |
|---|---|---|---|
| 5,581,677 A | 12/1996 | Myers et al. | |
| 7,002,580 B1 | 2/2006 | Aggala et al. | |
| 7,714,862 B1 * | 5/2010 | Dwyer et al. | 345/440 |
| 2003/0071814 A1 * | 4/2003 | Jou et al. | 345/440 |
| 2006/0070013 A1 * | 3/2006 | Vignet | 715/854 |
| 2006/0150122 A1 | 7/2006 | Hintermeister et al. | |
| 2007/0168154 A1 * | 7/2007 | Ericson | 702/179 |
| 2007/0208992 A1 | 9/2007 | Koren | |
| 2008/0005677 A1 | 1/2008 | Thompson | |
| 2008/0082908 A1 | 4/2008 | MacGregor | |
| 2009/0006241 A1 * | 1/2009 | Zhao et al. | 705/37 |
| 2009/0021517 A1 * | 1/2009 | Foslien | 345/440 |
| 2009/0287673 A1 * | 11/2009 | Chronister et al. | 707/5 |
| 2009/0300544 A1 | 12/2009 | Psenka et al. | |
| 2010/0049686 A1 | 2/2010 | Gotz | |
| 2010/0169137 A1 * | 7/2010 | Jastrebski et al. | 705/7 |
| 2010/0175006 A1 | 7/2010 | Li | |
| 2010/0262949 A1 | 10/2010 | Jacobsen et al. | |
| 2011/0004483 A1 | 1/2011 | Ting et al. | |
| 2012/0078522 A1 | 3/2012 | Avinash et al. | |
| 2012/0313949 A1 | 12/2012 | Rope et al. | |

(Continued)

OTHER PUBLICATIONS

D. Richard Cutler, Thomas C. Edwards, Karen H. Beard, Adele Cutler, Kyle T. Hess, Jacob Gibson, and Joshua J. Lawler, "Random Forests for Classification in Ecology", Nov. 2007, Ecological Society of America, vol. 88, Issue 11, http://www.esajournals.org/doi/abs/10.1890/07-0539.1.*

(Continued)

*Primary Examiner* — Ming Hon
*Assistant Examiner* — Sarah Le
(74) *Attorney, Agent, or Firm* — Yeen Tham; Edell, Shapiro & Finnan, LLC

(57) ABSTRACT

According to one embodiment of the present invention, a computer-implemented method comprises generating a plurality of charts to visually represent a multivariate data set, mapping variables within the multivariate data set to components of each chart, calculating a score value for each chart based on a plurality of factors, and presenting one or more of the plurality of charts based on corresponding score value.

15 Claims, 17 Drawing Sheets

(56) References Cited

U.S. PATENT DOCUMENTS

2014/0071138 A1     3/2014    Gibson et al.
2014/0198105 A1     7/2014    Gibson et al.

OTHER PUBLICATIONS

Morineau, "Visual Data Mining: the case of Vitamin System and other software.", 2004, Revue MODULAD 100.31 ,http://modulad.fr/archives/numero-31/morineau-31/morineau-31.pdf.*

Perer, Adam, and Ben Shneiderman. "Balancing systematic and flexible exploration of social networks." Visualization and Computer Graphics, IEEE Transactions on 12.5 (2006): 693-700.*

Tableau Software, "Tableau Show Me," kb.tableausoftware.com/articles/knowledgebase/autonnatic-show-me (viewed Mar. 1, 2012), 4 pages.

Jock MacKinlay, Pat Hanrahan, Chris Stolte, "Show Me: Automatic Presentation for Visual Analysis," IEEE Transactions on Visualization and Computer Graphics, vol. 13, No. 6, pp. 1137-1144, Nov.-Dec. 2007.

Martin Voight, Stefan Pietschmann, Lars Grammel, and Klaus Meissner, "Context-aware Recommendation of Visualization Components," eKNOW 2012: The Fourth International Conference on Information, Process, and Knowledge Management, IARIA 2012, ISBM: 978-1-61208-181-6, pp. 101-109.

Houssem Jerbi, Franck Ravat, Olivier Teste, and Gilles Zurfluh, "Applying Recommendation Technology in OLAP Systems," J. Fllipe and J. Cordiero (Eds.): ICEIS 2009, LNBIP 24, pp. 220-233, 2009.

David Gotz and Zhen Wen, "Behavior-Driven Visualization Recommendation," IUI'09, Feb. 8-11, 2009, Sanibel Island, Florida, USA. ACM 978-1-60558-331-0/09/02, pp. 315-324.

OSCI, "Case study: Practical steps for improving visualization," 2009, http://www.improving-visualisation.org/case-studies/id=7 (viewed Mar. 12, 2012), 11 pages.

Juice Analytics, Inc., Juice Labs-Chart Chooser, http://labs.juiceanalytics.com/chartchooser.html (viewed Mar. 1, 2012), 2 pages.

Stephen D. Gibson, "Determining Alternative Visualizations for Data Based on an Initial Data Visualization," U.S. Appl. No. 13/610,198, filed Sep. 11, 2012, 45 pages.

Daniel J. Rope, "Automatic Selection of Different Visualizations for the Organization of Multivariate Data," U.S. Appl. No. 13/550,985, filed Jul. 17, 2012, 38 pages.

* cited by examiner

AUTOMATIC SELECTION OF DIFFERENT VISUALIZATIONS FOR THE ORGANIZATION OF MULTIVARIATE DATA

BACKGROUND

1. Technical Field

Embodiments of the invention relate to the organization of data for visualization, such as visualization of data in the form of charts.

2. Discussion of the Related Art

Converting one or more sets of data into a visualization that adequately represents such data can be a challenging and difficult task even for experienced data analysts. For example, there are a significantly large number and variety of different types of parameters for an analyst to select from to present data in the form of a chart including, without limitation, chart dimensionality (e.g., a one dimensional chart, a two dimensional chart, a three dimensional chart, etc., with the further decision of which data values to map to which dimensions), types of charts (e.g., line charts, point charts, area charts, bar charts, pie charts, etc.), and how to map data to a particular chart (e.g., providing different line widths, dashed patterns, glyph shapes, colors, area fills, border patterns, etc.). The challenges become even more complex when faceting (also referred to as paneling or trellis) is utilized. For faceting, any number of variables can be used to create groups of charts in a table-like fashion. In a simple example of faceting, pie charts might be generated to show what proportion of a given population has certain income levels, with the chart being faceted by factors such as gender and age to produce a table of pie charts.

When there are only two or three variables in the data to display, there are a manageable number of visualization choices for the data. However, the possible choices increase exponentially with the addition of further variables to the data.

While certain visualization features for data (e.g., providing good color scales, suitable sizes, patterns, angles, etc.) are known, it becomes very difficult to manually construct decent charts for multivariate data that are both aesthetically pleasing and informative.

BRIEF SUMMARY

According to one embodiment of the present invention, a computer-implemented method comprises generating a plurality of charts to visually represent a multivariate data set, mapping variables within the multivariate data set to components of each chart, calculating a score value for each chart based on a plurality of factors, and presenting one or more of the plurality of charts based on corresponding score value.

Embodiments of the present invention further include a system and computer program product for implementing a method in substantially the same manner described above.

DETAILED DESCRIPTION

Figure 1:
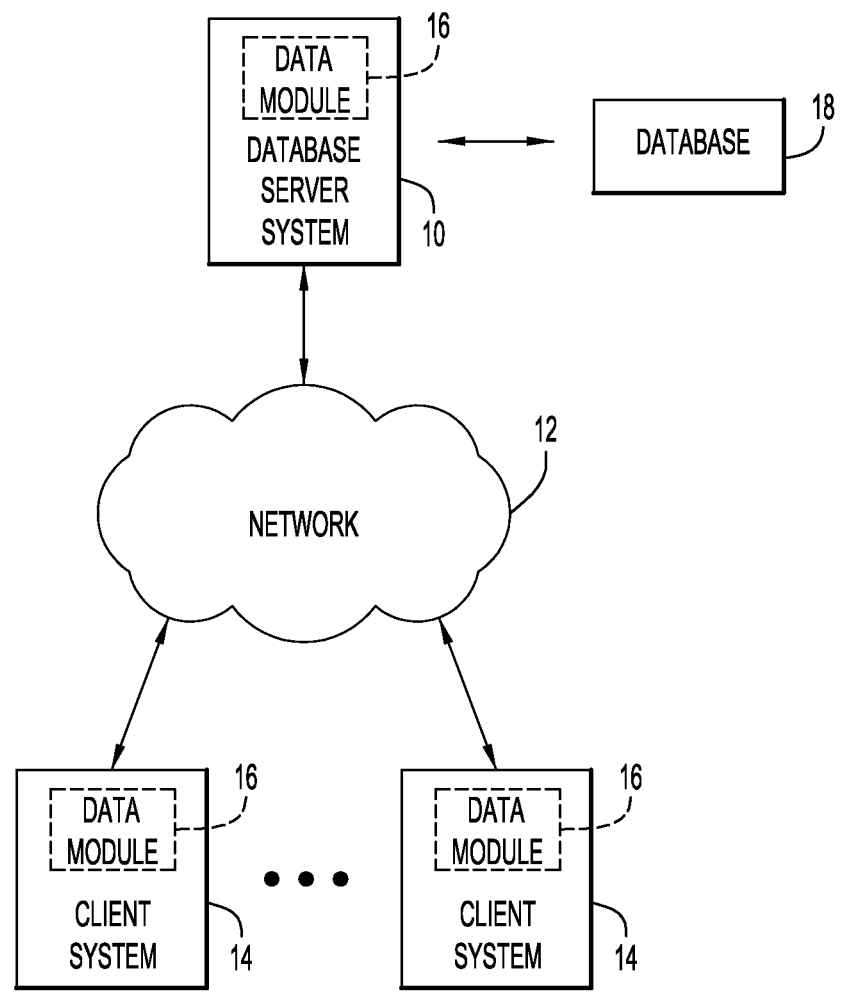
FIG. 1 is a diagrammatic illustration of an example computing environment for use with an embodiment of the present invention.

Present invention embodiments evaluate a multivariate data set and generate a plurality of charts or other visual representations to visually represent the data. Variables (e.g., a column or field within a database table) within the multivariate data set are mapped to components of each chart, and a score value is calculated for each chart based on a plurality of factors. A smaller subset of one or more charts or visual representations are presented from the plurality of charts or visual representations, where selection of which charts or visual representations to provide within the smaller subset is based upon the corresponding score value for each chart/visual representation. A user can then select from the smaller subset which one or more visual representations are most desirable for use. This results in less time and effort spent by the user to try to determine the best manner to display the data when starting from the initial data set.

In an example embodiment, the scoring of each generated chart is based upon the statistical strength of association between variables, how well each variable can be mapped to the chart based upon its assigned role, and an overall measure of chart complexity (e.g., based upon a predetermined complexity level of each chart).

The resultant ranking of generated charts can be presented to the user in some suitable presentation (e.g., a top ten list or other listing of a suitable number of generated charts having the highest or best rankings). The user can then choose one or more charts from the presentation. The user can further limit the search space for the generation of charts and/or the presentation of generated charts in any suitable manner (e.g., by requiring that a particular variable be located on the X-axis of a two dimensional chart), where the generated charts are ranked and presented to the user based upon the limitation implemented by the user. Generated charts that are related to user selected charts can also be linked with such selected charts and presented to the user. Thus, the user is presented with a smaller subset of all possible charts or visual representations for a particular set of multivariate data, reducing the complexity and time constraints associated with determining how to best visually display the data of interest to the user.

As used herein, the term "chart" refers to a visual representation of data from a data set, such as a multivariate data set, in which variables from the data set are mapped to a set of chart components. Examples of chart components include, without limitation, chart positions (e.g., X, Y, Z coordinates), chart aesthetics (e.g., color, size, labeling, shape, etc.) and faceting (e.g., rows, columns, outer rows, outer columns, etc. for a chart). It is noted, however, that the present invention embodiments are not limited to charts but instead are applicable to any number of different forms or types of visualizations or visual representations of data. The data set can include any selected number and types of variables. In an example data set using a relational model, a multivariate data set comprises a data table in which each record (i.e., each row of data) is described by a set of columns, where each column is a data variable.

Thus, the present invention embodiments facilitate the creation of a set of a significant number of or all possible mappings of data from a data set into visualizations, a scoring of the mappings, a return of a selected number (N) mappings, and presentation of the selected number of mappings as visualizations to the user. The user then has the ability to select which one or more visualizations to use.

In order to determine the best visualizations of data from a data set, the present invention embodiments provide an innovative and valuable technique for scoring a multivariate chart to determine its utility. To produce this score, the following basic building blocks can be utilized, which are described in further detail below:

1. Measures of association between variables. A simple measure for purely numeric fields would be statistical correlation, but this requires generalization for mixed numeric and categorical fields. In the present invention embodiments, a generalized association based on chi-squared statistical tables and a generalized association based on random forest statistical analysis are utilized to measure associations between variables.

2. Per-component measures of data suitability, which are based on statistical along with meta characteristics of the data (such as number of categories, skewness and uniformity), provide a measure of how suitable a given component is for a variable. For example, a categorical variable with 5 cases is more suited to be used for color than a skewed numeric variable.

3. A generalized model of complexity for components and combinations of components. For example, an X position component is easier to interpret than a color component. In addition, whereas one faceting component is relatively interpretable, two are much harder to interpret. In the present invention embodiments, this complexity model is a linear statistical model derived from a controlled experiment.

A weighted combination of factors such as these is used to generate an overall score, which can then be used to select the most informative charts from the possible ones. In practice, there are too many possible charts to evaluate all possibilities, and so the present invention embodiments additionally reduce the search space so as to evaluate only those charts with a greater likelihood of scoring high. Further, charts that contain similar variables are grouped together in a display, which allows a user to quickly review several related charts. Similarly, linked charts are also presented to the user with increasing numbers of variables included. This is similar to a "drill-down" technique; however, each step reveals charts containing actual relationships within the data.

Since, in practice, the number of possible charts is enormous, the basic algorithm must be modified so as to be usable. The basic technique for reducing the search space is to eliminate classes of charts that will not produce a good score. In particular, only variables that have a meaningful association are considered as candidates to use, and this eliminates charts that cannot show meaningful information and vastly reduces the search requirements. In addition, highly unsuitable mappings are not considered. For example, a binary variable would not be considered for a label, as far more informative mappings are possible.

An example environment for use with present invention embodiments is illustrated in FIG. 1. Specifically, the environment includes one or more server systems 10, and one or more client or end-user systems 14. Server systems 10 and client systems 14 may be remote from each other and communicate over a network 12. The network may be implemented by any number of any suitable communications media (e.g., wide area network (WAN), local area network (LAN), Internet, Intranet, etc.). Alternatively, server systems 10 and client systems 14 may be local to each other, and communicate via any appropriate local communication medium (e.g., local area network (LAN), hardwire, wireless link, Intranet, etc.).

Client systems 14 enable users to interact with server systems 10 for various applications. The server systems include a data module 16 to analyze multivariate data received from a database system 18 or other source in order to generate charts or other visual representations of the data and perform the further processing functions of narrowing the visual representations to a manageable level for review by a user. The database system may be implemented by any conventional or other database or storage unit, may be local to or remote from server systems 10 and client systems 14, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired data and analysis and may provide the visualizations. The graphical user (e.g., GUI, etc.) or other interface (e.g., command line prompts, menu screens, etc.) solicits information from a corresponding user pertaining to the desired data and analysis, and provides reports including generated charts as well as any other types of analysis results.

Server systems 10 and client systems 14 may be implemented by any conventional or other computer systems preferably equipped with a display or monitor, a base (e.g., including the processor, memories and/or internal or external communications devices (e.g., modem, network cards, etc.)), optional input devices (e.g., a keyboard, mouse or other input device), and any commercially available and/or custom software (e.g., server/communications software, analysis module, browser/interface software, etc.). In addition, data module 16 may include one or more modules or units to perform the various functions described below, and may be implemented by any combination of any quantity of software and/or hardware modules or units.

Alternatively, one or more client systems 14 may analyze data when operating as a stand-alone unit. In a stand-alone mode of operation, the client system stores or has access to the data, and includes a data module 16 to analyze the data.

Figure 2:
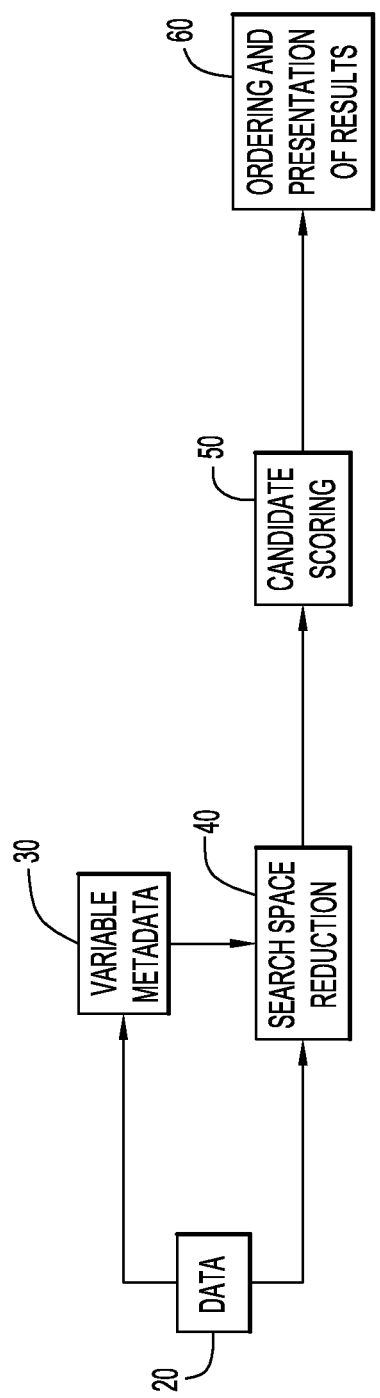
FIG. 2 is a flow diagram illustrating the manner in which data from a data set is analyzed to generate and present visualizations of data according to an embodiment of the present invention.

Data module 16 (e.g., via server system 10 and/or client system 14) analyzes data from a multivariate data set within database system 18 or other storage device in the manner as generally set forth in the flow diagram of FIG. 2 (and also the flow diagrams of FIGS. 3, 5, 6, 9, 10 and 13). In particular, a data set comprising multivariate data is provided for analysis by the data module 16 (step 20). As noted above, the data set can be stored within the database 18 and accessible over the network 12 by client system 14 for analysis by data module 16. Alternatively, the data set can be stored directly within the data module 16 for analysis. The data in the data set is methodically searched for the strongest statistical relationships using any information that is available in conjunction with examination of the actual records within the data set. The output is a large set of graphics that are specified and scored by the data module in the manner described below.

The data set undergoes a variable metadata analysis (step 30) to discern characteristics of each variable independently. The variable metadata analysis supplements any explicit metadata that might be available, and this information is useful for discerning relationships between variables in order to assess the most useful combinations of variables in generating visualizations. Since the possible number of visualizations is significantly large (e.g., a data set including just ten variables would result in millions of possible different visualizations of data), a reduction in the initial search space for generating visualizations is preferred. Thus, a search space reduction is performed (step 40) by combining the univariate metadata analysis step with statistical analysis of the data itself. The results are a set of candidate relationships between pairs of variables as well as more subtle relationships between a selected number of variables (e.g., up to five variables). At least a portion of the search space reduction (step 40) can be performed in parallel with the variable metadata analysis (step 30).

Even after reducing the initial search space to potentially meaningful relationships (in step 40), there are still an extremely large number of potential visualizations that could depict the discovered relationships. Therefore, a candidate scoring of the potential visualizations is implemented (step 50). The candidate scoring of the potential visualizations obtained after the search space reduction are further refined by: (1) examination of the importance of an individual variable within a given multivariate relationship combined with heuristic expert rules for constructing visualizations; and (2) preference for visualizations that are considered simpler to interpret based on a score calculated from a predictive model.

Intuitive presentation of the results to the user is helpful. An ordering and presentation of the results (step 60) is provided to the user with increasing numbers of variables for the visualizations. In addition, the ordering and presentation can include a navigational feature which allows the user to navigate between visualizations that are linked by the number of variables in common between them.

The process steps set forth in FIG. 2 are now described in further detail. In addition, an example data set is provided below (Table 1) in the form of a standard relational database table where each record (row) is described by a set of variables (columns). This data set is processed in accordance with the process steps outlined in FIG. 2 to generate and score visualizations of the data. The data set comprises a plain text (e.g., CSV format) file of data on automobiles, consisting of nine variables (columns). Only a selected number of records (rows) of the data are provided in the table for illustrative purposes, and it is understood that a data set can be analyzed and processed with the embodiments of the invention having any selected number of records. In an example implementation, a limit of five variables is imposed per chart/visualization. However, the invention embodiments are not limited to five variables, and any suitable number of variables can be utilized to generate visualizations based upon a particular data set or scenario.

TABLE 1

Example Data set (Data for Automobiles)

| mpg | engine | horse | weight | accel | year | origin | cylinder | filter_$ |
|---|---|---|---|---|---|---|---|---|
| 18 | 307 | 130 | 3504 | 12 | 70 | 1 | 8 | 0 |
| 15 | 350 | 165 | 3693 | 11.5 | 70 | 1 | 8 | 0 |
| 18 | 318 | 150 | 3436 | 11 | 70 | 1 | 8 | 0 |
| 16 | 304 | 150 | 3433 | 12 | 70 | 1 | 8 | 0 |
| 17 | 302 | 140 | 3449 | 10.5 | 70 | 1 | 8 | 0 |
| 15 | 429 | 198 | 4341 | 10 | 70 | 1 | 8 | 0 |
| 14 | 454 | 220 | 4354 | 9 | 70 | 1 | 8 | 0 |
| 14 | 440 | 215 | 4312 | 8.5 | 70 | 1 | 8 | 0 |
| 14 | 455 | 225 | 4425 | 10 | 70 | 1 | 8 | 0 |
| 15 | 390 | 190 | 3850 | 8.5 | 70 | 1 | 8 | 0 |
|  | 133 | 115 | 3090 | 17.5 | 70 | 2 | 4 | 1 |
|  | 350 | 165 | 4142 | 11.5 | 70 | 1 | 8 | 0 |
|  | 351 | 153 | 4034 | 11 | 70 | 1 | 8 | 0 |
| ... | ... | ... | ... | ... | ... | ... | ... | ... |

Variable Metadata Analysis

Figure 3:
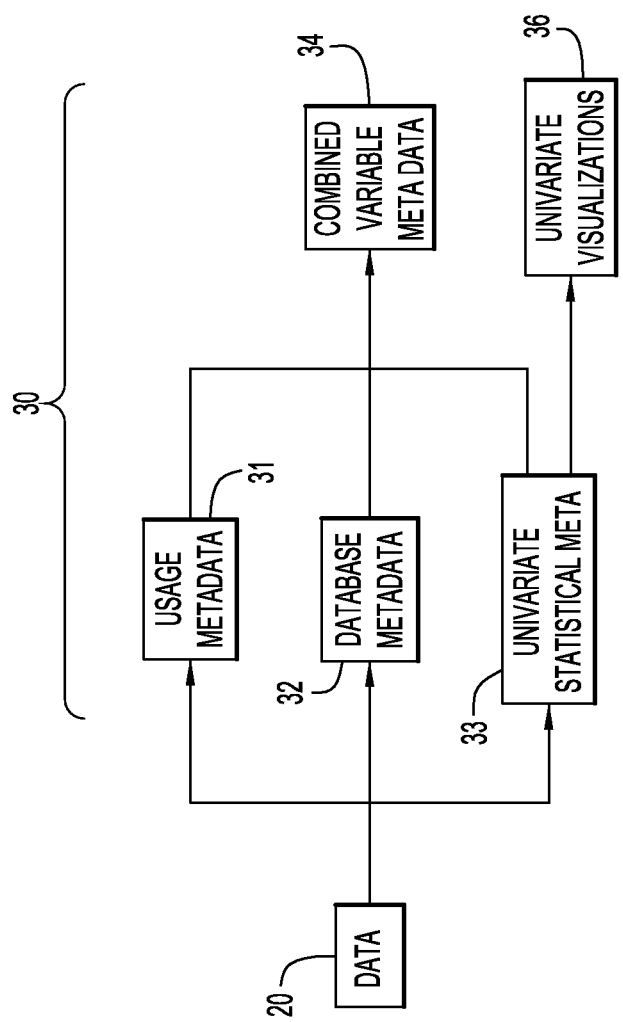
FIG. 3 is a flow diagram describing further steps associated with obtaining variable metadata from the flow diagram of FIG. 2 according to an embodiment of the present invention.

The variable metadata analysis (step 30) takes the data set (from step 20), which can be in the form of a data matrix or a database table (e.g., the data in Table 1), and evaluates each variable to generate two forms of output for each variable: (1) a set of meta data that describes the variable; and (2) a visual representation of the variable. An example implementation of the variable metadata analysis is shown in FIG. 3. In particular, the data is analyzed, independently for each variable (thus rendering the analyses parallelizable), utilizing a usage metadata analysis (step 31), a database metadata analysis (step 32) and a univariate statistical metadata analysis (step 33). An example implementation of performing the data analysis of these steps is to utilize parallel processing or a distributed analytic framework (built on cloud-computing, HADOOP, or similar environments). However, the processing steps can also be implemented by running the analyses for each variable within a single processing thread or any other processing system.

The usage metadata analysis (step 31) determines a suggested usage for certain variables of the data set. A visualization can be considered as a statistical model of the data. For example, the variable on a Y-axis of a chart is typically assumed to depend on a variable on the X-axis. Variables used to segment data, such as variables that are used to panel a chart or color points or lines of a chart, indicate a conditional relationship, where a Y variable depends on an X variable differently depending on the value of the conditioning variable. Thus, it is important to deduce the suggested usage for variables of the data set. The specific usage may be present or identified in existing metadata for a variable of interest. Alternatively, the usage may need to be imputed for the variable of interest. Usage metadata may include the following classifications: predictor/target classification; domain information classification; and type classification.

The predictor/target classification determines whether or not a variable should depend upon another variable (e.g., whether the variable should be placed on the Y axis) by preference. In the absence of existing metadata from the data set, the classification of predictor or target can be determined in any suitable manner. For example, the classification for a variable can be imputed by the following logic, which is based solely on the names of the variables:

1. A table of regular expressions is defined, where the table matches regular expressions to values indicating both whether the variable is likely to be a predictor or a target, and the strength of that likelihood. This table can be pre-determined, and can further be updated based upon a user's interactions with the client system 14 over a given time period.
2. Each variable name is compared to each entry in the table and, when matched, the weight for predictor or target likelihood is incremented.
3. For each variable, if the score for predictor is greater than that for target, and that score is higher than a pre-determined level, the variable is categorized as a predictor.
4. For each variable, if the score for target is greater than that for predictor, and that score is higher than a pre-determined level, the variable is categorized as a target.
5. If none of 1-4 are applicable to a variable, the variable is characterized as unknown.

The domain of a chart or other visualization can also be imputed using similar logic. A domain, in the context of a chart or visualization of data, is an area of data analysis (e.g., "time series", "banking", "e-commerce", etc.). This information is of secondary use in constructing charts/visualizations as certain domains have preferred charts (lines for economic time series, for example). It can also be used to improve the predictor/target classification by modifying the predictor/target weights assigned to variables based upon the specific domain. It is further noted that any other suitable number and/or types of categorical tags can be used in addition or as an alternative to predictor and target tags for a variable, where such categorical tags help to characterize usage of the variable based on the name associated with the variable.

The variables can be assigned types, including storage and measure types. The storage type of data can be, for example, double integer, string or date. The measure type of data can be, for example, ratio, ordinal or binary. For each variable, the appropriate storage type can be determined by examining the data. The measure describes the numeric properties of a variable and can be deduced using simple rules. For example, all double data can be assigned a ratio measure type. Integer data can be assigned a ratio measure type unless there are very few different values and they are all small, in which case a binary measure type (for 0/1 variables) or an ordinal measure type (for data that looks like a preference or rank scale—e.g. values {1, 2, 3, 4, 5}) can be assigned. Referring to the data set in Table 1, the storage type, measure type and usage type are assigned to the different variables of the data set as set forth in Table 2 below:

TABLE 2

Data Types and Usage for Variables of Table 1

| Name | Type: storage | Type: measure | Usage |
|---|---|---|---|
| mpg | Double | Ratio | target |
| engine | Double | Ratio | target |
| horse | Integer | Ratio | either |
| weight | Integer | Ratio | predictor |
| accel | Double | Ratio | predictor |
| year | Integer | Ratio | predictor |
| origin | Integer | Ordinal | predictor |
| cylinder | Integer | Ratio | predictor |
| filter_$ | Integer | Binary | predictor |

The database metadata analysis (step 32) copies any metadata present in the original data set (from step 20) into the output metadata. If existing metadata for a particular variable obtained from the data set can be used to determine metadata that has been imputed from other variable metadata processing steps (e.g., predictor/target classification and/or statistical measures), such database metadata should be used instead of imputation for that variable.

The univariate statistical metadata analysis (step 33) independently calculates statistical descriptive data for each variable. This processing step includes standard statistical measures such as mean, standard deviation, count, missing value count, skewness, kurtosis, order statistics (median, quartiles, etc.) as well as a special indicator comprising a flag that is marked as true when the variable is determined to be an identifier. This is the case when a variable has unique values of strings or integers, with each data row including a unique value. These variables will not be mapped to components of a chart except for textual components.

In addition, a bounded-size summary of the data is created suitable for use in creating a statistical chart. For categorical data, this summary comprises a table of frequencies for the unique categories of a variable, while ensuring that at most a fixed number of categories (for example, a maximum of 100 categories) occurs by aggregating all the lowest frequency items into a single "other" category for the categories whose frequencies do not fall in the top fixed number (e.g., the top 100).

For numeric data, the same frequency table is generated, except that statistical binning is used to create frequencies for ranges of values. For example, variable-sized bins can be formed (utilizing a variable-bin histogram algorithm or any other suitable method) to generate a fixed number of bins for a variable (e.g., a maximum number of bins being 100).

Referring again to the data set of Table 1, a univariate statistical metadata summary for the "year" variable is shown in Table 3 below:

TABLE 3

Univariate Statistical Metadata Analysis for "Year" Variable

| Value | Frequency |
|---|---|
| 0 | 1 |
| 70 | 34 |
| 71 | 29 |
| 72 | 28 |
| 73 | 40 |
| 74 | 27 |
| 75 | 30 |
| 76 | 34 |
| 77 | 28 |
| 78 | 36 |
| 79 | 29 |
| 80 | 29 |

TABLE 3-continued

Univariate Statistical Metadata Analysis for "Year" Variable

| Value | Frequency |
|---|---|
| 81 | 30 |
| 82 | 31 |

As can be seen in Table 3, the data for "year" has only 14 different values, with many values repeated, so the summary is exact. For data with over a set number (e.g., 100) different values, data can be binned into smaller bins so that the fixed limit of bins will not be exceeded. Suppose, for example, the "year" variable is to be bound to only five bins, the data could be binned as shown in Table 4 below:

TABLE 4

Highly Binned Univariate Statistical Metadata Analysis for "Year" Variable

| Value | Frequency |
|---|---|
| 0 | 1 |
| 70.93 | 91 |
| 73.90 | 97 |
| 77.02 | 98 |
| 80.53 | 119 |

Figure 4:
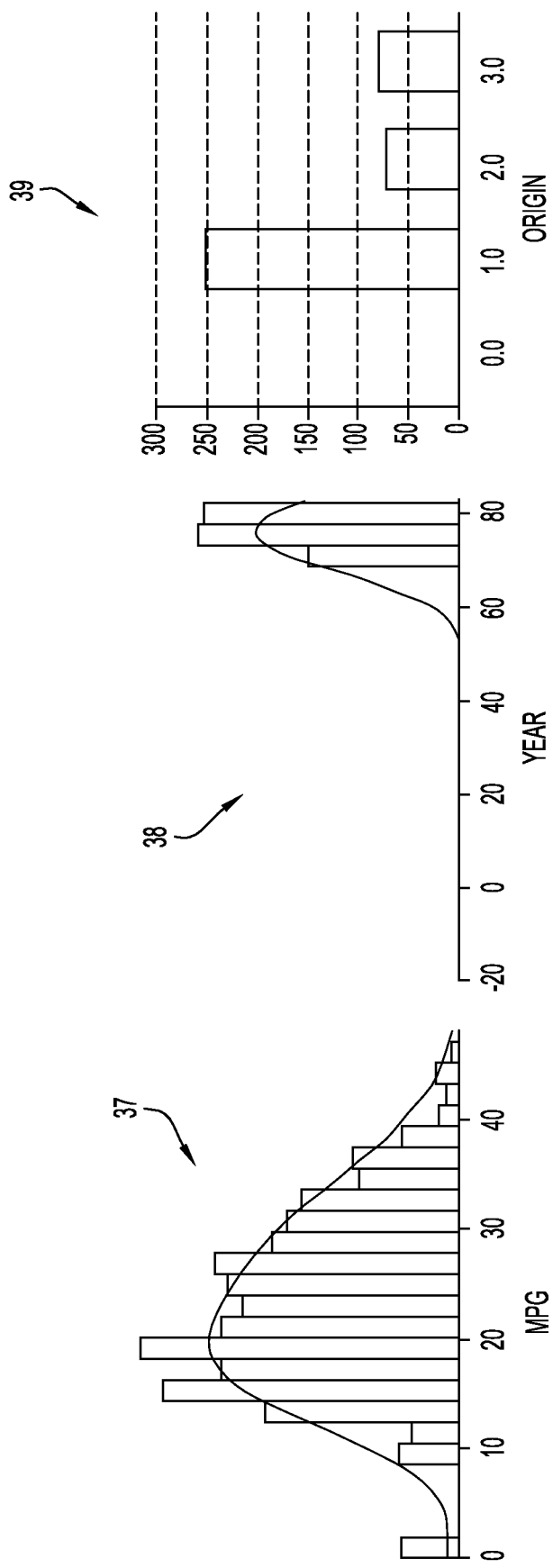
FIG. 4 depicts a plurality of charts showing univariate representations of three variables from a data set according to an embodiment of the present invention.

The univariate statistical metadata (from step 33) is used to generate univariate visualizations of the data (step 36), using standard graphical statistical algorithms. In an example implementation, a bar chart can be generated for a variable with a string type or a small number of integer values (categorical data), while a histogram can be generated with density smooth for time data, double data or data with a large number of integer categories (numeric data). Examples of both types of charts are shown in FIG. 4. In particular, histograms 37 and 38 are depicted for the statistical metadata for the variables "mpg" and "year" from the data set of Table 1, while a bar chart is generated for the statistical metadata for the "origin" variable. Although "origin" has a storage type of integer, the same as "year", the metadata discovery gives it a different measure (ordinal rather than ratio). For ordinal data, a bar chart is generated instead of a histogram.

Search Space Reduction Analysis

Figure 5:
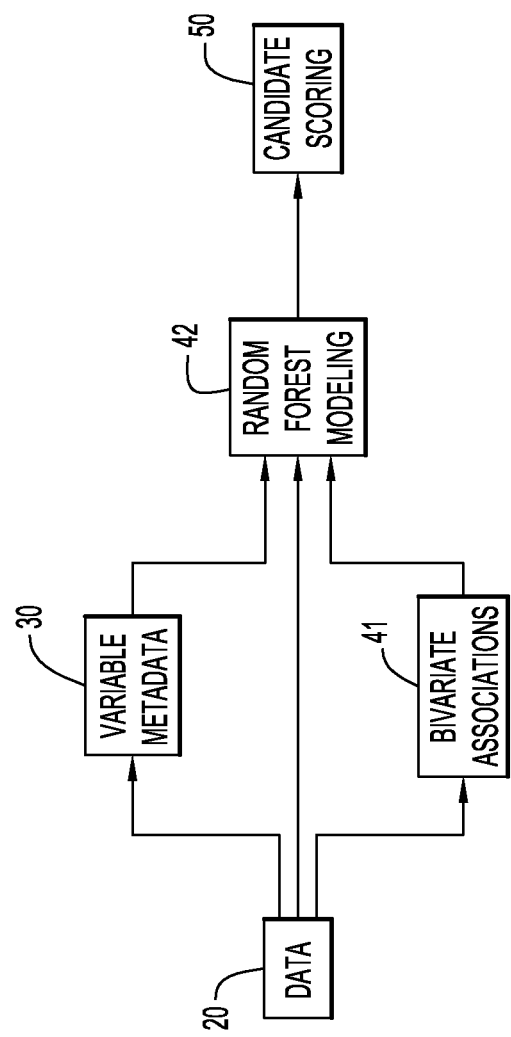
FIGS. 5 and 6 are flow diagrams describing further steps associated with search space reduction from the flow diagram of FIG. 2 according to an embodiment of the present invention.

The search space reduction analysis (step 40) is important to achieve a manageable set of results to present to the user. FIG. 5 shows in further detail the process steps associated with the search space reduction analysis, where statistical analysis is used in combination with the variable metadata results from the variable metadata analysis (step 30) to find the strongest relationships between variables of the data set. These relationships serve as a basis of consideration for multivariate visualizations.

The search space reduction analysis begins with a bivariate associations analysis (step 41), in which the strongest relationships between pairs of variables are determined. Variables with strong associations to other variables are given priority for the next processing step of random forest modeling (step 42). Random forest modeling determines relationships between more than two variables. As can be seen from FIG. 5, and as described in further detail below, the starting criterion for selecting candidate models for the random forest modeling includes information from both the variable metadata analysis (step 30) as well as the bivariate relationships analysis (step 41). Each model constructed as a result of the random forest modeling includes a set of variables with a known statistical relationship that is used to generate candidate visualizations.

Figure 6:
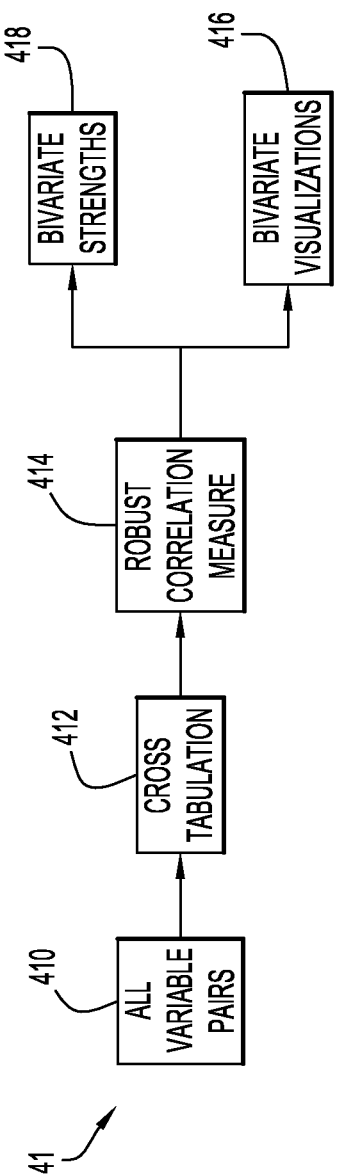

The bivariate associations analysis (step 41) is described in further detail with reference to FIG. 6. In particular, data taken from the data set (provided in step 20) is analyzed such that all variable pairs are evaluated (step 410) to produce two forms of output for each pair: (1) a measure of the strength of the relationship and a measure of its statistical likelihood; and (2) a visual representation of the relationship. The data is analyzed independently for each pair of variables. For example, the processing can be achieved by parallel processing or distributed analytic framework (e.g., processing built on cloud-computing, HADOOP software, or similar environments). Alternatively, the processing can be implemented running all the analyses for each pair of variables within a single processing thread. Since the analysis for each pair is independent, the computations can be parallelized using any of a suitable number of known or other techniques.

A bounded-size cross-tabulation table (step 412) is generated that defines the frequencies of each set of paired values that occur in the data. This cross-tabulation table defines the joint distribution of the pair of variables in the same way the frequency table defines the distribution of a single variable. The table is analyzed to provide two measures of the association: (i) a robust correlation measure to determine the statistical probability that the relationship is real (step 414); and (ii) the strength of the relationship (step 418), measured as the improvement in variance explained. The two calculated measures are saved for later use. The cross-tabulation table is used to create a bivariate visualization (step 416).

The technique for evaluating strengths is a non-standard process and provides several advantages over traditional statistical methodology for calculating strengths of relationships between variables. It provides the advantage that it allows relationships between categorical and continuous variables to be compared easily, as well as the implementation advantage that once the cross-tabulations have been performed, the resulting analysis is not dependent on the scale of the data, and so has fixed computational time for a given number of variables. The details of the algorithm are described below.

For large number of variables, the resulting number of pairs can become overly large. Therefore, that analysis can be limited to the generation of a fixed number of bivariate visualizations, choosing those with the highest strengths of relationships which are statistically significant.

The generation of a cross-tabulation table is described in greater detail as follows. As previously described, each variable of the data set can have a bounded-size frequency representation calculated, whether numeric or categorical. This results in defining at most a given number of bins (numeric or categorical) for each variable. Therefore, a pair of variables will define a table with a bounded number of cells (for example, given a limit of 100 categories per variable, this results in at most 10,000 cells for a pair of variables). The algorithm iterates through the data, and, for each pair, calculates the cell defined by the intersection of the bin for a first variable (variable 1) and the bin for a second variable (variable 2). The frequency for that cell is then incremented. For data with fewer than the number of bounded categories (e.g., 100 categories), the cross-tabulation table will be a perfect representation of the true bivariate distribution. Utilizing the example data set of Table 1, with the selection of a "year"/ "origin" variable pair, a cross-tabulation table would be generated as shown in Table 5 below:

TABLE 5

Cross-Tabulation For Year X Origin

| Origin | Year | | | | | | | | | | | | | |
| --- | --- | --- | --- | --- | --- | --- | --- | --- | --- | --- | --- | --- | --- | --- |
| | 0 | 70 | 71 | 72 | 73 | 74 | 75 | 76 | 77 | 78 | 79 | 80 | 81 | 82 |
| 1 | 0 | 26 | 20 | 18 | 29 | 15 | 20 | 22 | 18 | 22 | 23 | 7 | 13 | 20 |
| 2 | 0 | 6 | 5 | 5 | 7 | 6 | 6 | 8 | 4 | 6 | 4 | 9 | 5 | 2 |
| 3 | 0 | 2 | 4 | 5 | 4 | 6 | 4 | 4 | 6 | 8 | 2 | 13 | 12 | 9 |
| (missing) | 1 | 0 | 0 | 0 | 0 | 0 | 0 | 0 | 0 | 0 | 0 | 0 | 0 | 0 |

For efficiency, the cross-tabulation can be generated such that zero values are not stored, with only non-zero combinations being recorded.

The cross-tabulation between variable pairs becomes an approximation when the data are more diverse than this. The choice of a binning algorithm for numeric data will strongly affect the utility of this technique. In an example implementation, variable-width bins are used so that the marginal bin frequencies are more uniform and therefore more useful for analysis than fixed-width bins will be, in the case of highly non-uniform data.

The variable metadata (from step 30) can be used to indicate which variable is used for the Y dimension and which is used for the X dimension, with target variables on the Y dimension and predictors on the X dimension, by preference.

In the robust correlation measure (step 414), the cross-tabulation table is analyzed using standard analysis of variance (ANOVA) techniques for a two way table. The chi-squared measure is used to calculate the statistical probability that the relationship is real. The strength of the relationship is evaluated as the proportion of variance explained (the square root of the fraction SSE/SSTO in standard ANOVA terms).

The robust correlation measures of the data are calculated using the standard statistical chi-squared test for independence. For example, unlike a parametric test which would be confused by the presence of the unusual value '0' in the "year" variable for the cross-tabulation of Table 5, the chi-squared test based on the bins works well. It produces two measures. The first is the statistical significance, which is 0.64% (p=0.0064) so there is strong evidence there is a relationship. Also, the relationship allows a prediction of 80.3% of the variation in the counts (measured by dividing SSE, the sum of squared error terms when using the marginal frequencies to predict the counts, by SSTO, the sum of squared error terms when assuming all cells have equal frequencies).

The bivariate visualizations (step 416) are generated in the following manner. The cross tabulation data is used directly to calculate the following standard statistical plots, with the type of plot determined by the types of variable. Some example implementations of standard statistical plots are as follows:

1. Numeric by Numeric: a binned scatterplot is generated, where a dot is drawn for each cell location, the size (or color or brightness or luminosity) of which is in proportion to the cell frequency count.
2. Numeric by Categorical: a multivariate box-plot is generated with one boxplot for each category of the categorical variable.
3. Categorical by Categorical: a heatmap is generated for the table.
4. Numeric by Time: a time series chart is generated, with the value for the numeric variable at each time point determined by the mean of the cells for that marginal time.
5. Categorical by Time, Time by Time: A binned scatterplot is generated, as described above.

Figure 7:
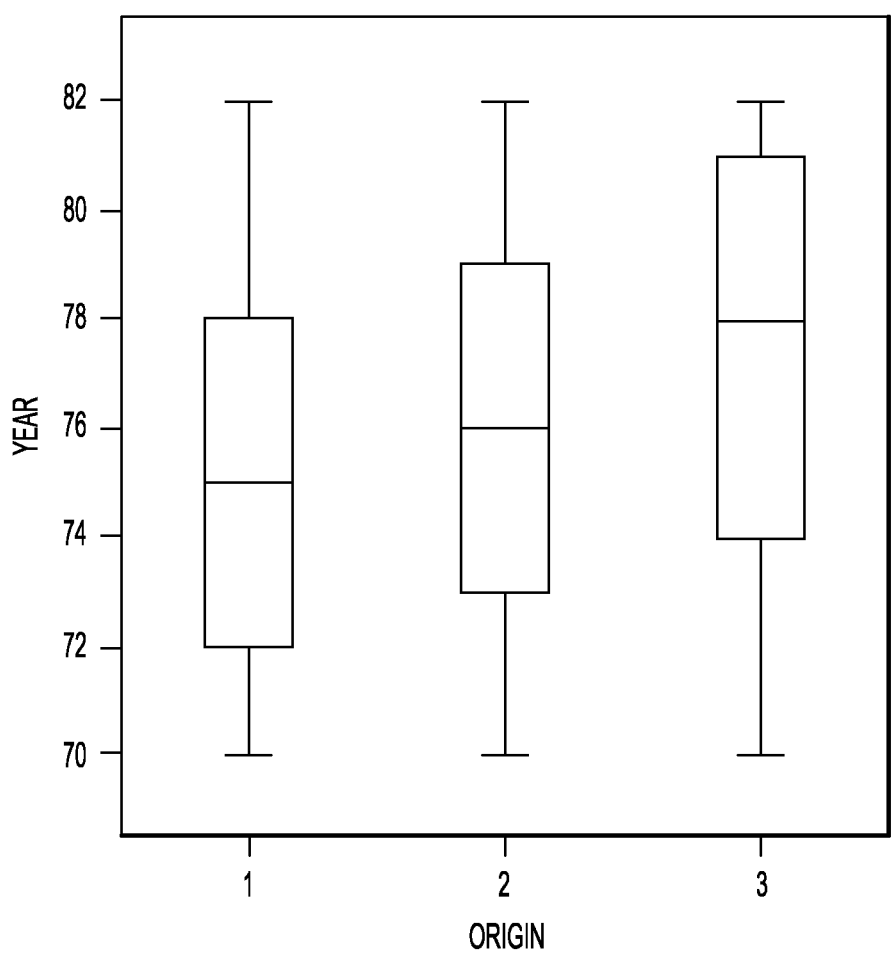
FIGS. 7 and 8 are charts showing two bivariate views of data associated with two variables of a data set according to an embodiment of the present invention.
Figure 8:
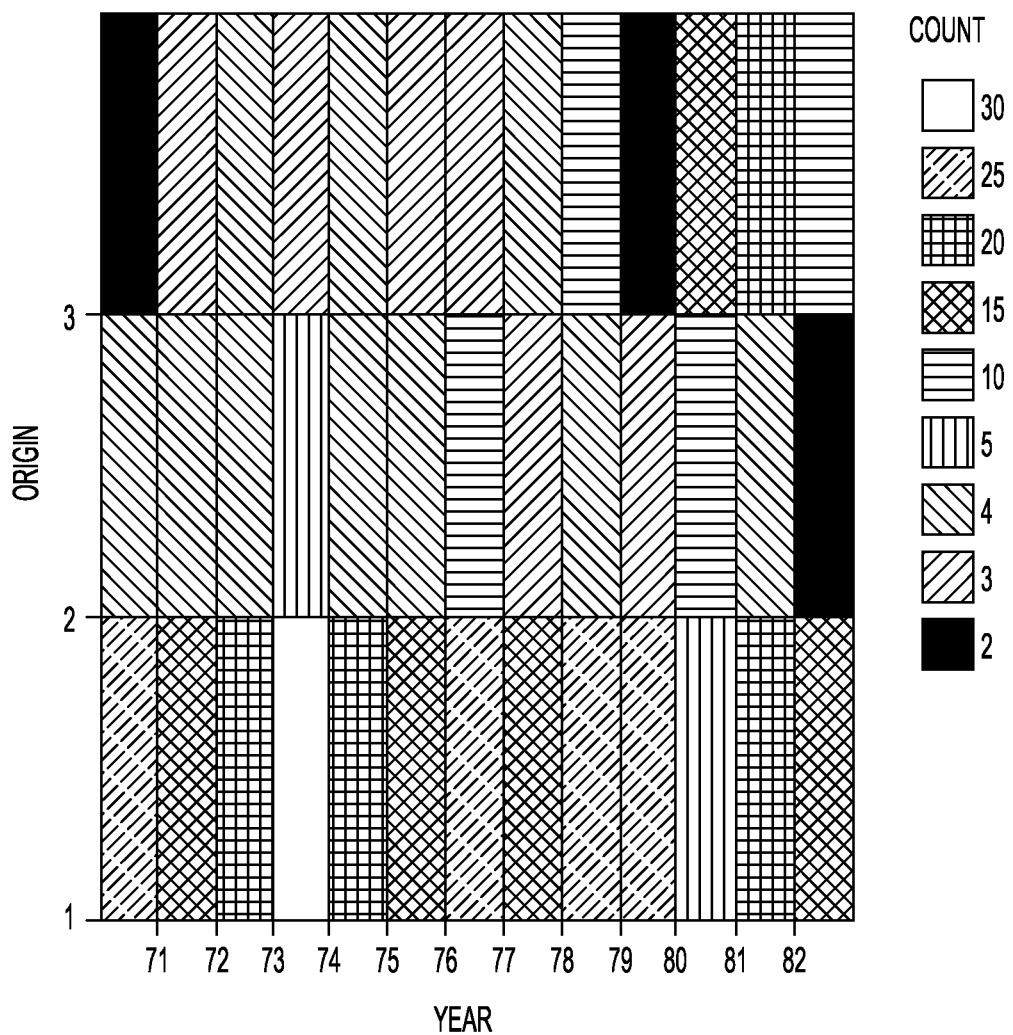
Figure 9:
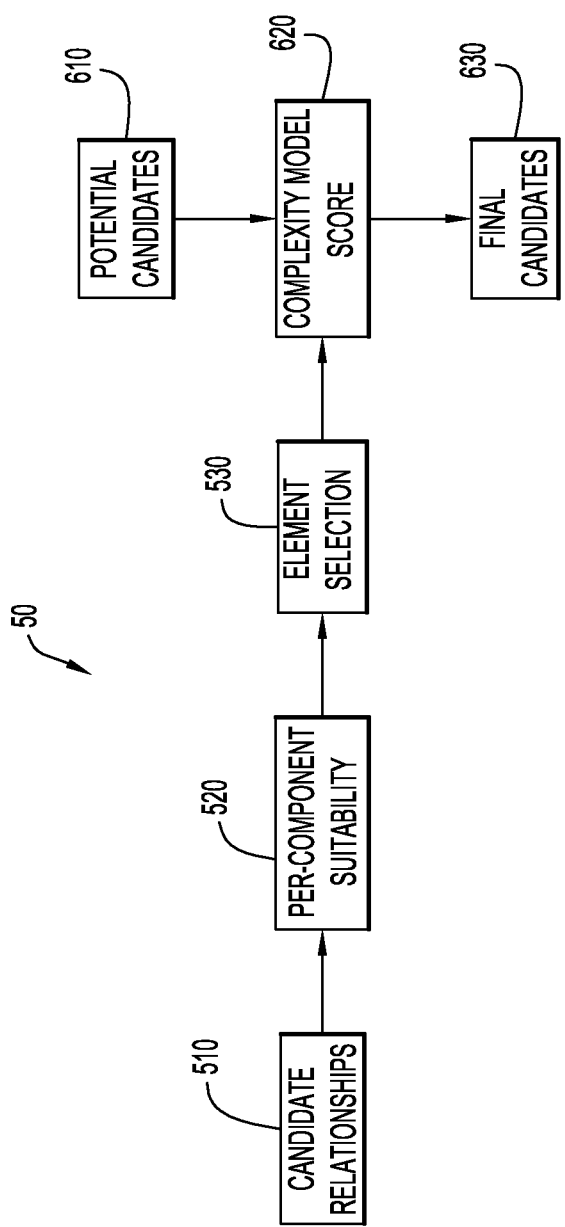
FIGS. 9 and 10 are flow diagrams describing further steps associated with candidate scoring and ordering and presentation of results from the flow diagram of FIG. 2 according to an embodiment of the present invention.
Figure 10:
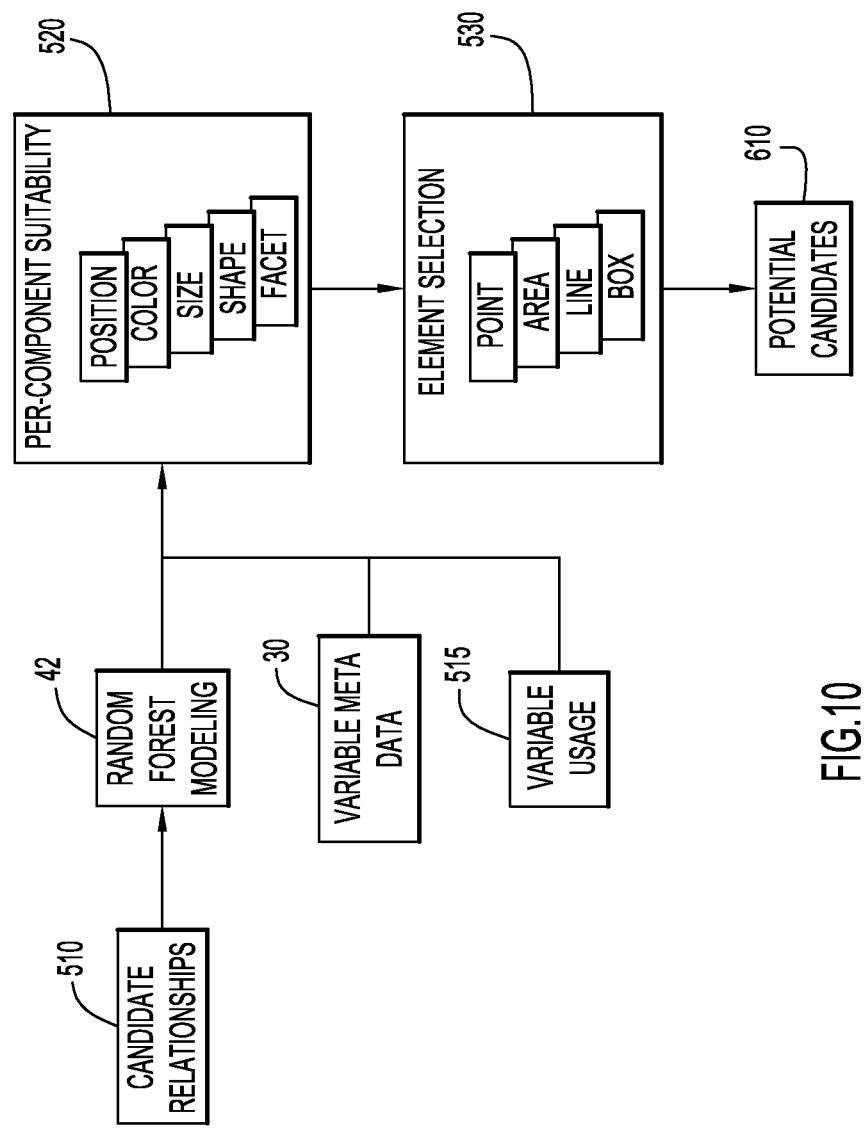

Two example bivariate visualizations utilizing the variable pair data of the "year"/"origin" pair from Table 5 are depicted in FIGS. 7 and 8. Referring to FIG. 7, a boxplot of the data is depicted in FIG. 7, while a heatmap of the data is depicted in FIG. 8 (where the different cross-hatching in boxes represents different colors associated with a different count that could be presented in a color display of the heatmap). The boxplot is preferable based on the ratio nature of the "year" variable. The heatmap would be an alternative if the "year" variable was classified as ordinal or categorical.

Random Forest Modeling

The overall goal of the invention embodiments is to construct meaningful visualizations of data from a data set. While it might be useful to consider all possible subsets of variables and choose those that are meaningful, it is infeasible to construct all possible subsets of variables except for small numbers of variables. Therefore, the standard statistical technique of "random forests" is utilized as a surrogate for the "all-subsets" approach. The steps involved with this approach are as follows:

1. For each variable Y, build a random forest model that predicts this variable using a subset of the other variables.
   a. Use the variable metadata to ensure that only variables with usage "unknown" or "predictor" are used to predict a variable.
   b. If there are a large number of such variables (enough to make fitting the model overly long), choose those variables with the greatest strengths of relationships with the target variable, using the association data calculated during the bivariate associations (step 41).
2. For each model, record (i) the statistical probability that the relationship is real; and (ii) the strength of the relationship, measured as the improvement in variance explained.
3. If the model is statistically valid, record the contribution of each variable X to the model for the target variable Y. This can be done in a number of ways, such as those described for standard or typical random forest models. In an example implementation, the model is re-fit with the variable X excluded from the model, and the difference in strength of relationship is used as the contribution measure. The result of this step is, for each variable, a list of other variables that are associated with this variable in a multivariate sense, ordered and scored by their contribution to the multivariate model.

The following example is a summary report for a sample tree from the forest used to predict the variable "mpg" from the data set of Table 1. This model predicts the variable "mpg" using 6 other variables. The model explains 78.36% of the variation in the target. The model used is a decision tree model (CHAID), which builds a set of decision points based on the predictor variables to decide the value of the target variable. The tree built has 52 nodes and is 6 levels deep. This model has an accuracy of 78.36%, which means that about that much percentage of the variation in "mpg" is explained by the model. This model has a complexity of 52, which roughly indicates how many mathematical parameters are needed to describe this model.

The variable importances calculated to predict "mpg" are as follows:

0.46: accel (Double/Ratio/predictor)
1.59: cylinder (Integer/Ratio/predictor)
7.23: horse (Integer/Ratio/either)
0.13: origin (integer/Ordinal/predictor)
0.67: weight (Integer/Ratio/predictor)
2.81: year (Integer/Ratio/predictor)

The example summary report states that when building multivariate charts, with "mpg" as a target variable, the most important variable to use is "horse", followed by "year", then "cylinder", and so on.

Candidate Scoring

Candidate scoring (step 50) is the last step in the process of selecting, defining and scoring candidates for visualization is to further refine the choices by applying a combination of expert heuristics along with a classification of simplicity to the available candidates. The candidate scoring is described in further detail with reference to FIGS. 9 and 10. The random forest modeling results contain several predictive models, each of which has several variables. Even with decent expert heuristic rules, there are still many ways to combine these variables into visualizations, so there is still a rather large space of candidates. A scoring mechanism is provided to select simpler, yet diverse visualizations of the data.

Most systems that attempt to automatically produce or score visualizations from arbitrary data accomplish the task by examining how well the variables match the requirements of a fixed set of known visualizations. For example, variables such as gender, income and marital status would be scored against a representation of a bar chart, line chart, scatter plot or other predefined visualization. The embodiments of the invention match the best representation of a variable with the best component of a visualization.

The random forest modeling (step 42) defines a set of variables that are known to have a relationship (step 510). The variables in this model as well as the variable metadata (obtained from step 30) are utilized to facilitate obtaining several multi-dimensional visualizations beginning with assigning a per-component suitability (step 520) in the following manner:

1. Automatically assigning the target variable to the Y-axis as this most closely represents what the model is teaching.

2. Automatically assigning each of the remaining predictor variables a preferential order of aesthetic or positional usage (step 515) based on the rules shown in the following Table 6:

TABLE 6

Preferential Usage Order for Predictor Variables

| Importance | Number of Categories | Measurement Level | Aesthetic Usage Order |
|---|---|---|---|
| High | High | Numeric | X, Color, Size |
| High | High | Set | X, Color |
| High | Low | Numeric | X, Size, Facet-Y |
| High | Low | Set | X, Facet-X, Facet-Y |
| Low | High | Numeric | Color, Size |
| Low | High | Set | Color, X |
| Low | Low | Numeric | Facet-X, Color |
| Low | Low | Set | Facet-Y, Color |

An example application of these rules to variables in the data set of Table 1 is shown in Table 7 below:

TABLE 7

Preferential Usage Order for Predictor Variables for Table 1 Data set

| Name | #1 | #2 | #3 |
|---|---|---|---|
| mpg | x | color | size |
| engine | x | color | size |
| horse | x | color | size |
| weight | x | color | size |
| accel | x | color | size |
| year | x | color | facet |
| origin | color | facet | shape |
| cylinder | x | color | facet |
| filter_$ | facet | shape | color |

Based on the above rules, when a multivariate relationship involving "mpg" with three other variables is a potential candidate, the following logic applies:

According to the bivariate and random forest processing steps, the top variables to use will be (in order): "horse", "year", "cylinder"

Using the above tables, the candidate choices of variables and representation are as follows (with a probable worst choice given at the end of the list):

"mpg": position, "horse": position, "year": color, "cylinder": facet

"mpg": position, "horse": position, "year": facet, "cylinder": facet

"mpg": position, "horse": position, "year": facet, "cylinder": color

...

"mpg": size, "horse": color, "year": x, "cylinder": y

Element selection (step 530) for the visualizations is achieved in the following manner. Specifications for visualizations starting with three variables and proceeding up to five variables are generated depending on the number of variables present in the statistical model and those variables with the highest importance. In an example embodiment, an algorithm can be utilized for element selection that uses the following heuristic rules that emulate how a visual expert might construct visualizations from the data.

For each target variable in the model:

1. Create a base bivariate visualization specification using a routine similar to that described above for bivariate associations (step 41) by pairing with all X-Axis candidates.

2. For each bivariate visualization specification, create a 3-variable visualization using each Color variable.

3. For each color visualization from Step 2, create a 4-variable visualization using each Size variable.

4. For each color visualization from Step 2, create a 4-variable visualization using each Facet X variable.

5. For each faceted visualization from Step 4, create a 5-variable, 2-way faceted visualization using each Facet Y variable.

These particular rules yield a wide variety of visualizations depicting different multivariate relationships. Some additional heuristic rules can also be included in this example implementation including, without limitation:

Add a smooth line to visualizations with point elements.

Dual encode color along with shape to provide greater visual distinction between categories.

Since some representations such as faceting require categorical data, any continuous data requested as a facet is automatically categorized into five levels.

The results of element selection are not actual renderings of visualizations but instead specifications of visualizations that can easily be evaluated further in the next step in the process.

Figure 11:
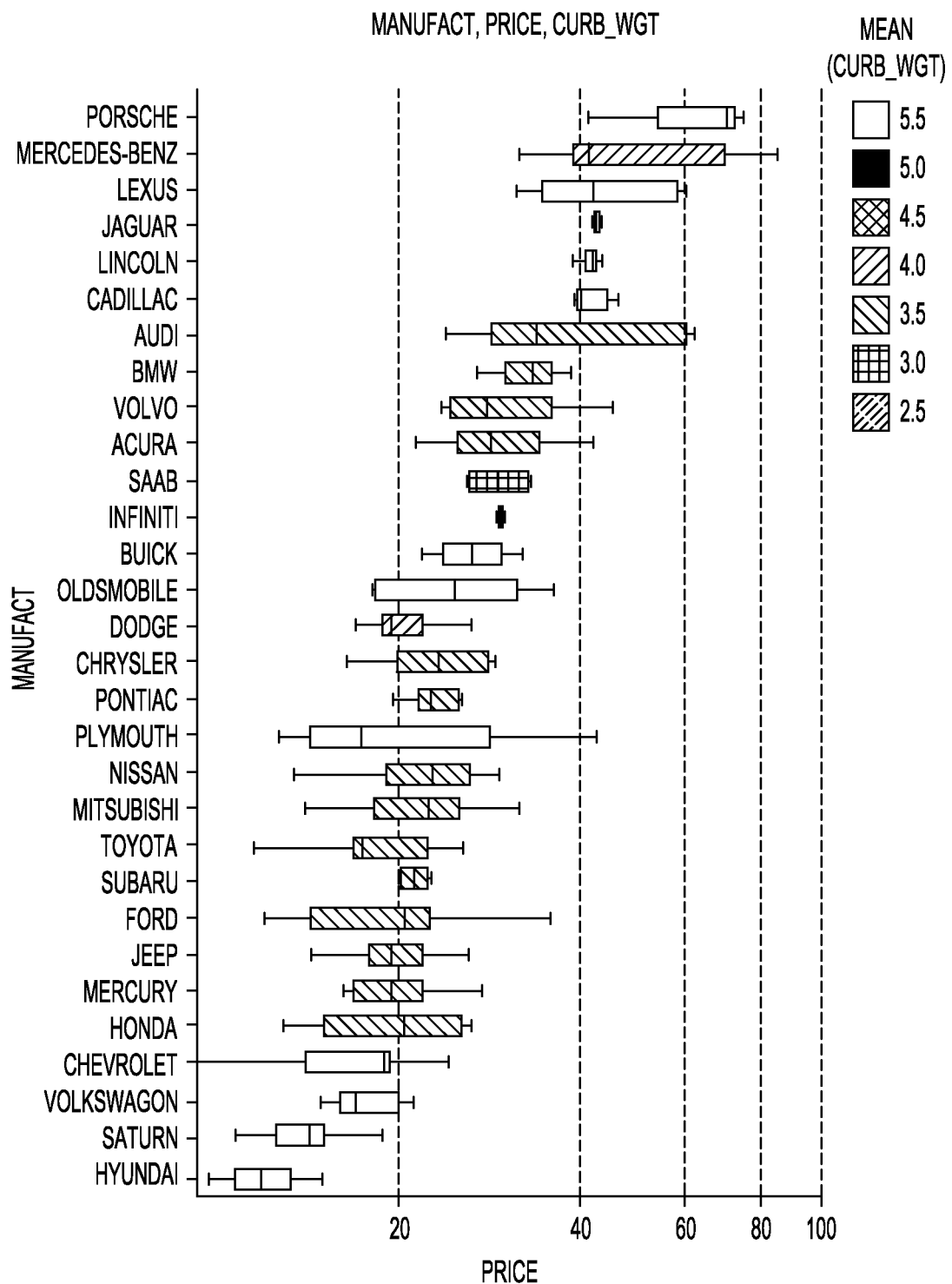
FIG. 11 is a chart showing a multidimensional visualization of data from a data set according to an embodiment of the present invention.

An example of a multidimensional visualization of data from the data set which results as output from this process is depicted in FIG. 11. The input is a data set about automobiles (e.g., a data set including the data of Table 1) with multiple variables including miles per gallon (mpg), prices, and manufacturer. The visualization in FIG. 11 is generated because manufacturer and weight are some of the factors that can predict the price of a car. Since manufacturer is categorical, a box is selected as the visualization element and color is a preferred choice for displaying the weight (where the different colors are represented by the different types of cross-hatching shown in the figure). Even though price is the target variable, it appears on the X-axis instead of the Y-axis because transposing the graph improves legibility.

Figure 12:
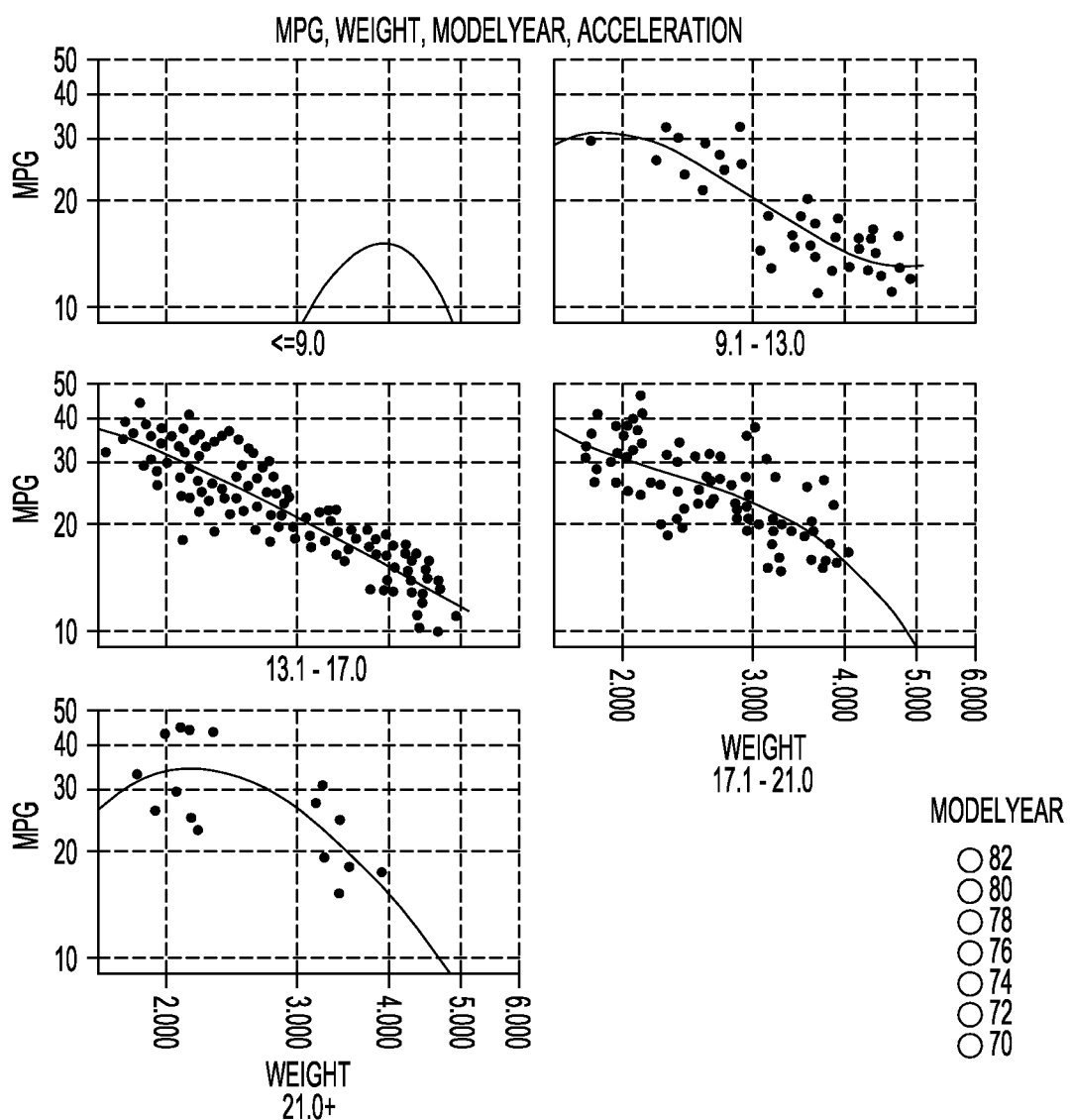
FIG. 12 depicts a plurality of charts showing a univariate representation of data from a data set where one data variable is a facet for the charts according to an embodiment of the present invention.

A second example of a multidimensional visualization of the same input data as that for FIG. 11 is depicted in FIG. 12. In this example, the weight, model year and acceleration are factors in predicting the miles per gallon of a car. Since weight is the largest factor, the x-axis position is preferred for this variable. The model year is a color variable. Although not specifically shown in FIG. 11 (since the figure is black and white), the different data points would have different colors in a color display of the data, where the different colored data points are referenced to a particular model year based upon the key provided in the figure. Acceleration was selected as a facet variable. However, since acceleration is continuous, five levels of acceleration (i.e., five box charts with acceleration ranges that increase between adjacent box charts) were automatically generated.

Ordering and Presentation of Results

Figure 13:
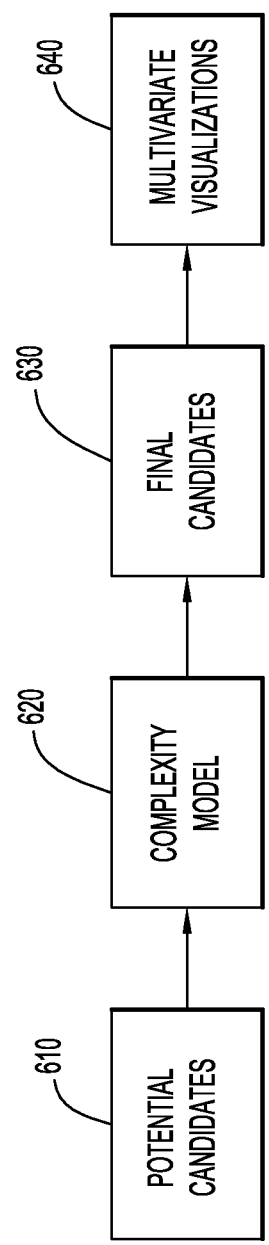
FIG. 13 is a flow diagram describing further steps associated with ordering and presentation of results from the flow diagram of FIG. 2 according to an embodiment of the present invention.

The ordering and presentation of results (step 60) is further described with respect to FIG. 13. Potential candidates (step 610) are obtained by taking a set of descriptions of potential multivariate visualizations. The potential multivariate visualizations are scored based upon a complexity model (step 620) that scores the visualizations by their relative complexity, a measure of how easy it is for users to interpret them, and uses this to filter down to a set of final candidates (step 630). The final candidates are then visualized (step 640). The details of these steps are described below.

The complexity of a visualization is modeled (step 620) using a statistical model, where the predictors of complexity in the model are counts of numbers of graphical elements present. For example, a two-way paneled scatterplot with a variable used for color would have position=1, facets=2, aesthetics=1 (for the five variables in the multivariate description). A simple time series chart would have position=2, facets=0, aesthetics=0. The statistical model is pre-built based on experience, a user study or other technique. In an example implementation, a linear regression model can be constructed using data from a user study. However, any modeling technique can be used so long as it allows any multivariate visualization description to be scored.

The algorithm to choose the final candidates (step 630) takes into account the complexity model (step 620), but does not simply pick the best or least complex visualizations. Instead, the final candidates algorithm performs the following steps iteratively:

1. Pick the highest scored model from the list of potential candidates.

2. For each other model, reduce the score for that model based on how similar it is to the model chosen. In the preferred implementation this is accomplished as follows:

a. The similarity, S, is calculated as the number of common variables divided by the average of the number of variables in the two candidates, a value between 0 and 1.

b. The score for the other model is reduced by a fixed multiple of S (0.25)

3. Repeat the process until all remaining models have scores below zero.

The final candidates algorithm described above ensures that a representative set of candidate models are chosen. This ensures that the best candidates are selected, subject to a "diminishing returns" policy that reduces the usefulness of candidates that are similar to ones already selected.

The candidate visualization (step 640) describes the mapping from variables to grammatical constructs, as described above for per-component suitability (step 520) and element selection (step 530). This is used directly to construct a chart using a suitable charting system. The element choices and positional variables can be used to define the basic chart type, then color, size and shape variables are used to modify that chart. Finally the variables assigned to facet are used to panel the chart.

Figure 14:
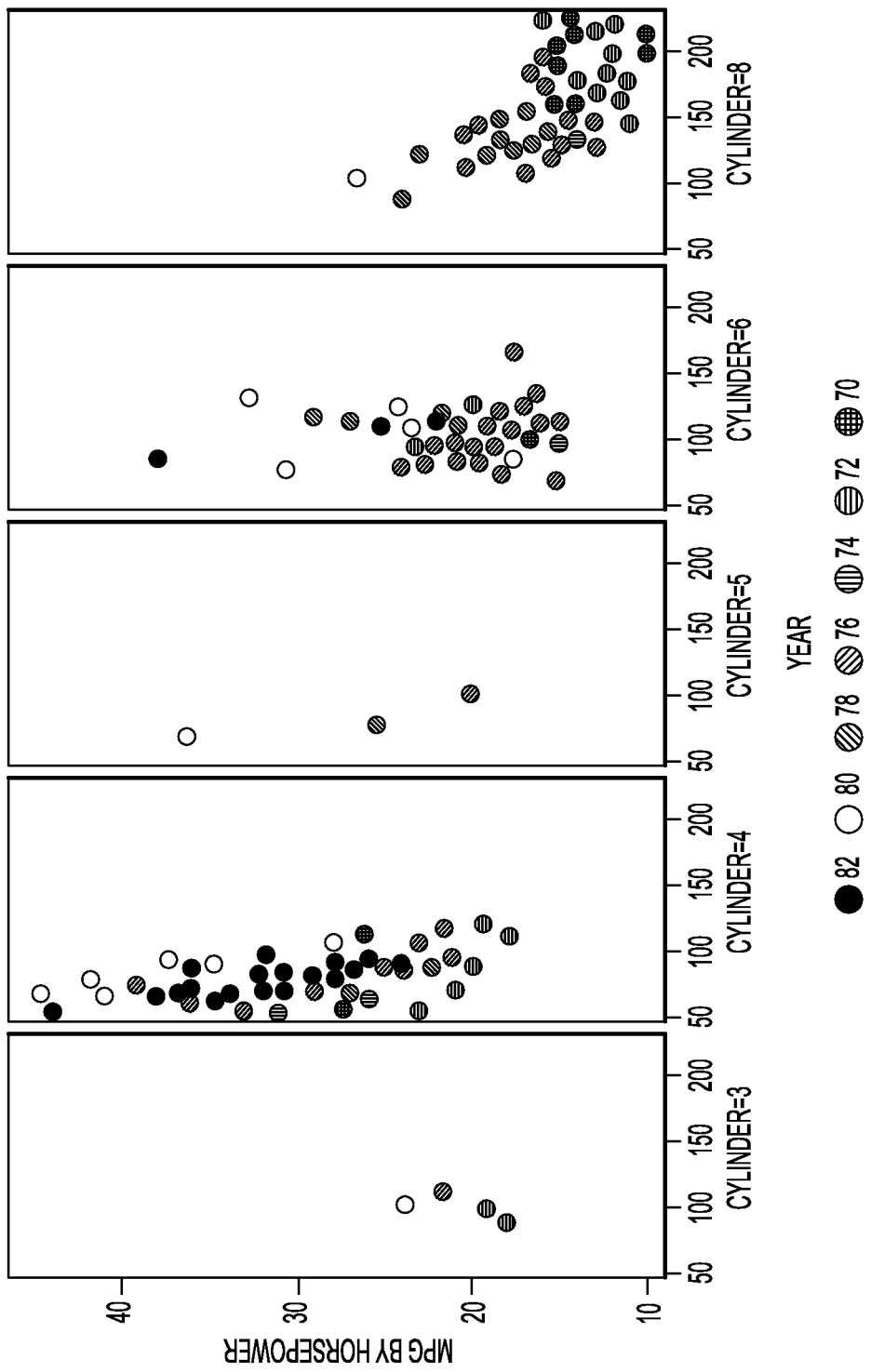
FIG. 14 is a chart showing a best multivariate choice visualization of data for a variable in combination with three other variables from a data set according to an embodiment of the present invention.

An example candidate visualization utilizing the data set of Table 1 is depicted in FIG. 14. In particular, FIG. 14 provides box charts generated based upon a multivariate choice obtained from the candidate visualization in which the variables "mpg", "horse", "cylinder" and "year" are displayed from the data set. In particular, the variables are plotted such that "horse" is an X-axis variable, "mpg" is a Y-axis variable, "year" is a color variable (where the different cross-hatchings shown in the figure represent different colors for the data points), and "cylinder" is a facet variable. The complexity model (step 620) evaluates the potential candidates from the data set forth in Table 7, obtained during the candidate scoring (step 50). The "winner" is selected based on a combination of this scoring and the ranking set forth in Table 7. In this example, the first ranked candidate ("mpg") scored sufficiently well to become the final choice. This multivariate visualization shows that there is a negative association between an automobile's miles per gallon rating and its horsepower and also that mpg tends to be lower in cars with more cylinders. However, as can be seen from the box charts of FIG. 14, more recent models (i.e., models in which the variable "year" is greater) have improved mpg even for automobiles with more cylinders. This visualization can be selected and constructed by the process described above without any specification or direction from a user (i.e., where only the data from the data set has been provided as input).

The previously noted processing steps generate a wide variety of potentially useful visualizations about the data input to the data module 16 from a data set. However, a user needs to complete the process by selecting which of the visualizations are indeed the most useful (e.g., based upon a user's particular needs or preferences). To facilitate this, the preferred implementation presents the generated multivariate visualizations to the user graphically. An example implementation of providing generated multivariate visualizations to the user graphically is as follows:

1. The user peruses all variables and collects relevant visualizations.

2. The system applies automatic ordering of the collected visualizations.

3. The user refines the automatic collection into the final results.

Figure 15:
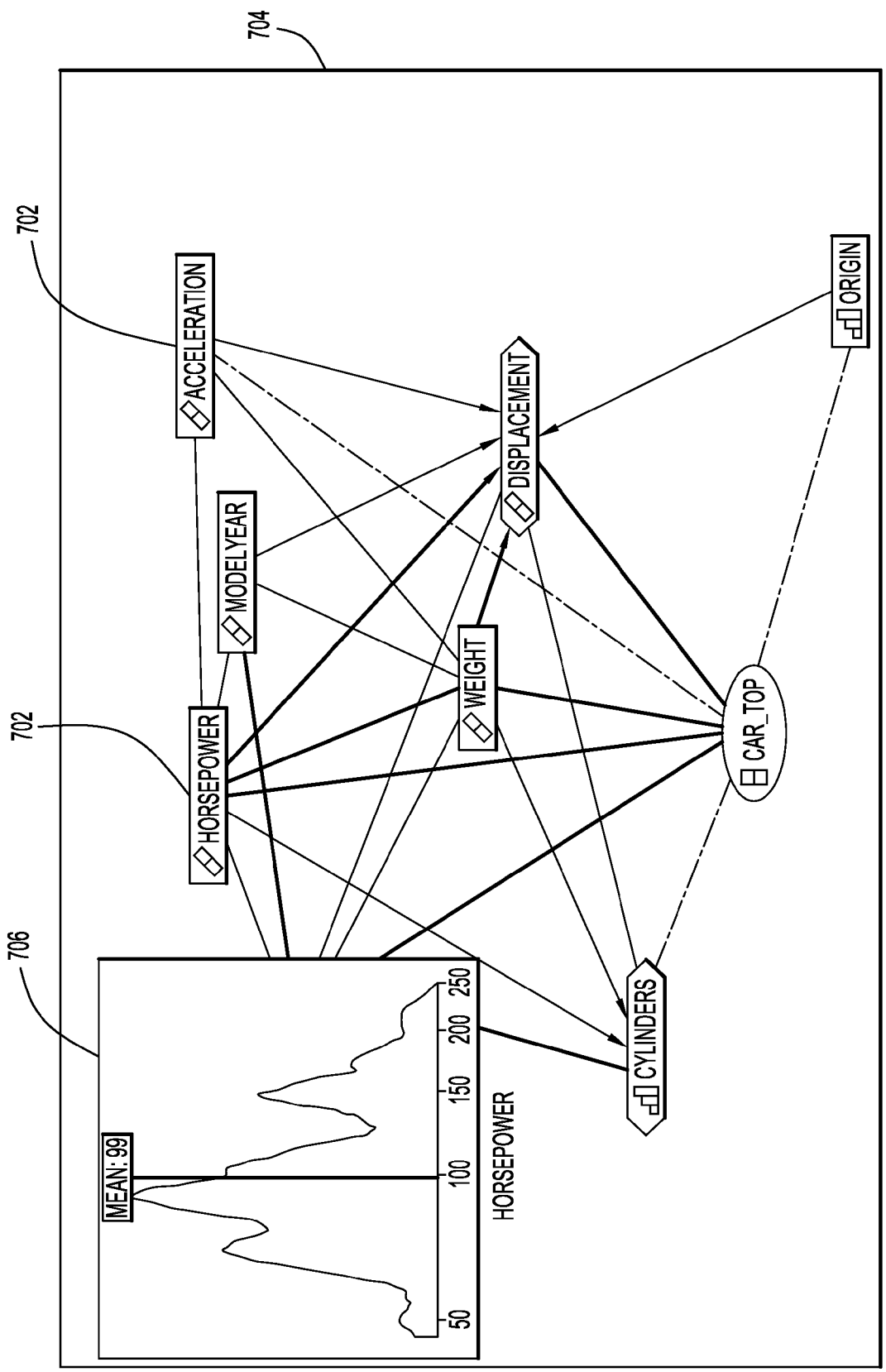
FIG. 15 is a navigational graph layout of variables from a data set represented as nodes with connections to represent bivariate relationships between nodes according to an embodiment of the present invention.

For the first step, the variables can all be arranged in a graph layout of a GUI, for example, a GUI display as depicted in FIG. 15. Each variable in the data is displayed as a node (e.g., node 702 for "acceleration") in the graph and the line connections represent the strength of the bivariate relationship (e.g., line connection 704 extending between the "acceleration" and "displacement" nodes). The graph is interactive such that the user can hover over the nodes to reveal a visualization of the variable distribution or the links to see the bivariate relationship. For example, as shown in FIG. 15, a variable distribution plot 706 is displayed when the user hovers over the "horsepower" node 702.

Figure 16:
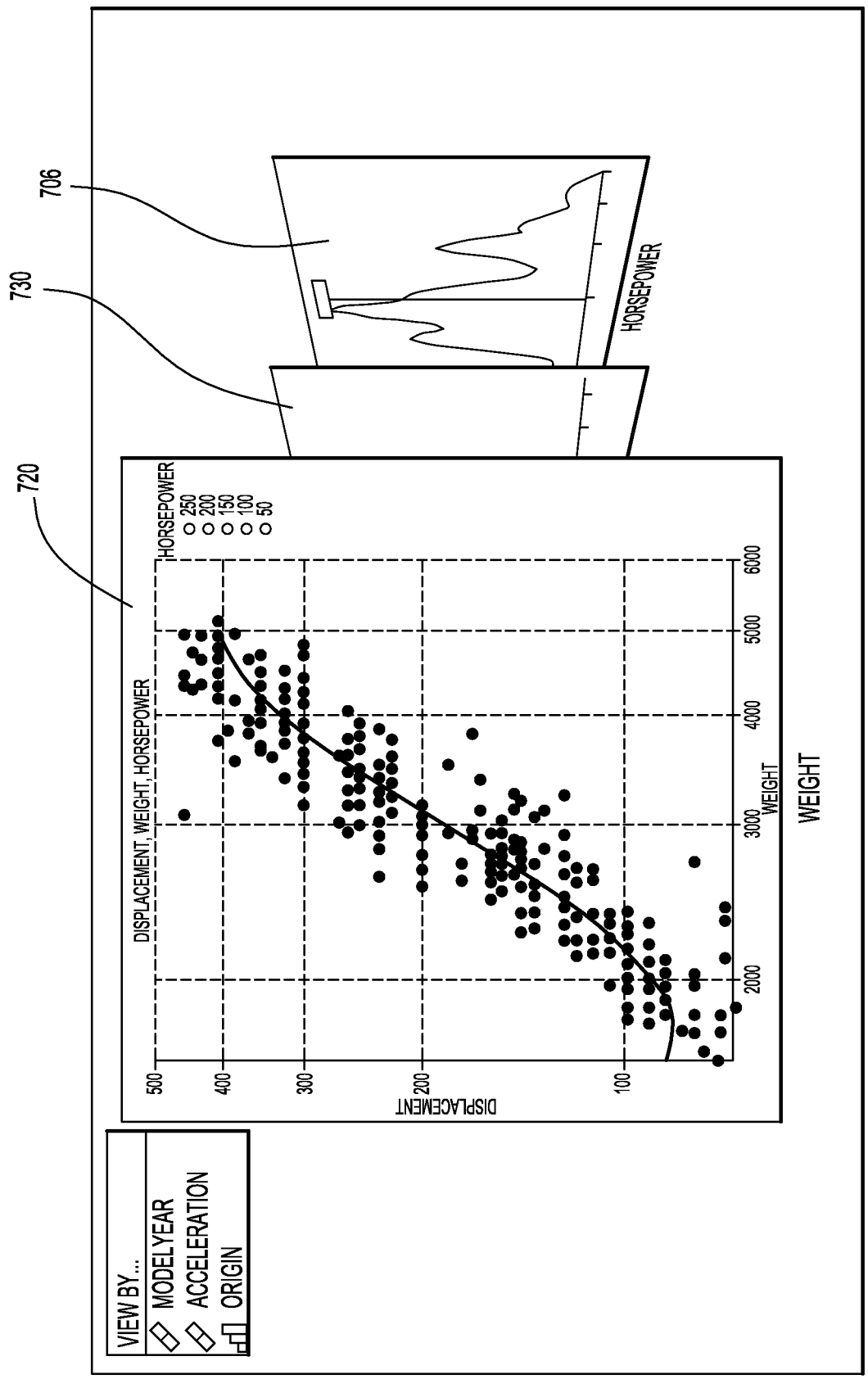
FIGS. 16 and 17 are charts that plot multivariate data for variables of interest selected from nodes of the navigational graph layout of FIG. 15 according to an embodiment of the invention.

Selecting a variable at a node 702 from the graph layout of FIG. 15 navigates the user to a sub-screen that allows the user to examine related visualizations. An example sub-screen to which a user can navigate from the graph of FIG. 15 is shown in FIG. 16. In particular, the graph 720 in FIG. 16 shows a plot of horsepower and its relationship with displacement and weight variables, where displacement (Y-axis) is plotted vs. weight (X-axis) with horsepower as a color variable.

For each visualization, variables are presented to the user where more visualizations are known to exist that have meaningful statistical relationships. Each selection adds a new variable to the picture and can further provide a different visual representation of the variables. The user simply marks any of the visualizations to include in the final presentation. The user can then return to the original graph layout of FIG. 15 and repeat the process using a different starting variable (i.e., selecting a different node and navigating to display different relationships of the variable associated with that node).

Figure 17:
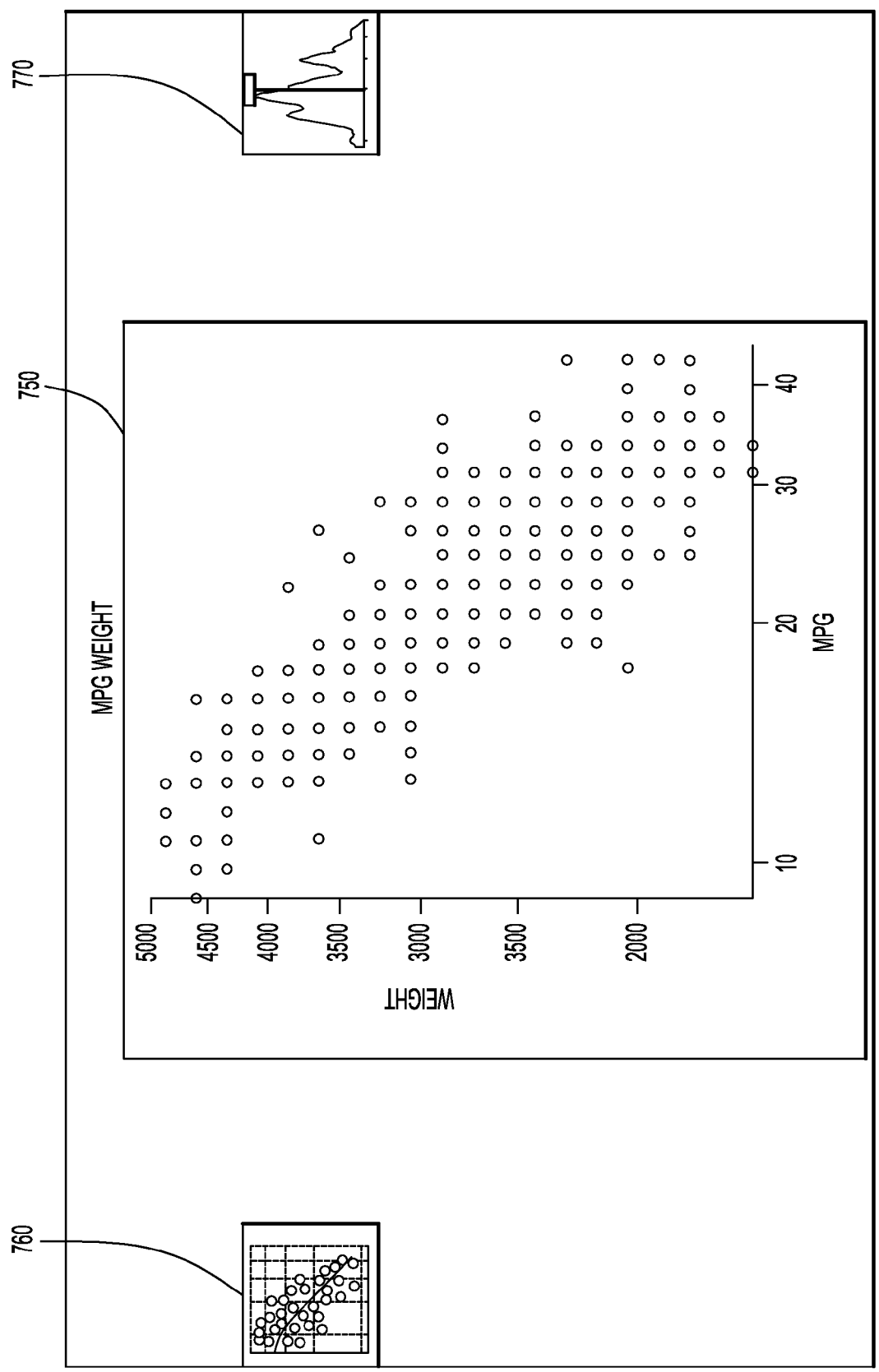

In the second step, all selected visualizations are assembled into a unified presentation. Connections are automatically added between the selected visualizations by calculating the number of variables in common between the visualizations and providing thumbnail links to visualizations with similar variables. This is shown in FIG. 16, in which the user can navigate to other graphs 730 and 706. Another display is shown in FIG. 17, in which the user can navigate from a graph 750 to a graph shown as thumbnail 760 or another graph shown as thumbnail 770.

The final step by the user is to simply delete unneeded or unwanted visualizations and refine the linkages between the visualizations as desired.

Thus, the process described above can be implemented by the data module 16 of the server system 10 and/or the client system 14 to rapidly construct statistically relevant multidimensional visualizations of data from a data set into an interactive presentation.

Other example implementations of the ordering and presentation of results are also possible. For example, a simple hierarchical menu system can be implemented, where the system starts by presenting the variables themselves, with the ability immediately to show univariate views of those variables. Those bivariate relationships which have been identified as significant can then be displayed (alternatively, they can be shown simultaneously with the variables themselves). The ability to view the bivariate views for those relationships is immediate. By drilling down on an n-dimensional view (n>=1), the user is always presented with a set of higher-dimensional views (m-dimensional views where m>n) that have been identified as significant, and where the set of variables in the m-dimensional view is a superset of those in the base n-dimensional view. This ordering technique allows the user to explore the space of significant multivariate views in an intuitive and statistically reasonable fashion.

Thus, the present invention embodiments automatically generate a plurality of charts or other visualizations of data from a multivariate data set and provide a user with a smaller subset (based upon a ranking or scoring of the initial set of visualizations) to consider, which results in providing statistically relevant multidimensional visualizations of the data while minimizing the time and effort that would otherwise be required by the user to try to determine the best manner to display the data.

It will be appreciated that the embodiments described above and illustrated in the drawings represent only a few of the many ways of implementing embodiments for automatic selection of different visualizations for the organization of multivariate data.

The topology or environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., IBM-compatible, laptop, PDA, mobile devices, etc.), and may include any commercially available operating system and any commercially available or custom software (e.g., browser software, communications software, server software, cleansing and data quality analysis software, etc.). These systems may include any types of monitors and input devices (e.g., keyboard, mouse, voice recognition, etc.) to enter and/or view information.

It is to be understood that the software (e.g., data module of the client systems and database system) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow diagrams may be modified in any manner that accomplishes the functions described herein. In addition, the functions in the flow diagrams or description may be performed in any order that accomplishes a desired operation.

The software of the present invention embodiments (e.g., data module of the client systems and database system) may be available on a recordable medium (e.g., magnetic or optical mediums, magneto-optic mediums, floppy diskettes, CD-ROM, DVD, memory devices, etc.) for use on stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data, regression model and corresponding parameters, rules, etc.). The database system may be implemented by any number of any conventional or other databases, data stores or storage structures (e.g., files, databases, data structures, data or other repositories, etc.) to store information (e.g., data, regression model and corresponding parameters, rules, etc.). These systems may be included within or coupled to the server and/or client systems. The database systems and/or storage structures may be remote from or local to the computer or other processing systems, and may store any desired data (e.g., rules, regression model and corresponding parameters, data to be analyzed, etc.).

Present invention embodiments may be utilized for analyzing the data of any types (e.g., boolean, character, alphanumeric, symbols, etc.) representing any information. Further, present invention embodiments may be utilized for analyzing data from any types of storage units, systems or devices (e.g., databases, files, memory devices, data structures, processing devices, various types of stationary or mobile computer or processing systems or devices, etc.). The data set analyzed from one or more data sets may be of any size, and include any type of data and metadata.

Any desired quantity or type of features or characteristics may be selected for the data set (e.g., length of token, type of token, etc.), where any quantity of any type of meta-features (e.g., any statistical characteristics of the selected features, location of storage, etc.) may be utilized for the data quality estimate. The features and meta-features may be represented by any type of values (e.g., boolean, alphanumeric, numeric, character, symbol, etc.).

The present invention embodiments may employ any number of any type of user interface (e.g., Graphical User Interface (GUI), command-line, prompt, etc.) for obtaining or providing information (e.g., obtaining information for the desired analysis to be performed, providing charts or other data visualizations, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for analyzing and generating visualizations of data from any data source for any type of process.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java (Java and all Java-based trademarks and logos are trademarks of Sun Microsystems, Inc. in the United States, other countries, or both), Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed:

1. A system comprising: a computer system including at least one data module configured to:
   generate a plurality of charts that visually represent data from a multivariate data set, wherein the generating a plurality of charts includes initially reducing a search space of potential chart candidates to be considered for presentation based on a corresponding score value by analyzing metadata associated with the multivariate data set in combination with statistical analysis of the data to determine relationships between variables of the multivariate data set, the determination of relationships between variables of the multivariate data set including a bivariate analysis that determines strengths for combinations of pairs of variables and a random forest model analysis that determines relationships between more than two variables;
   map variables within the multivariate data set to components of each chart;
   calculate a score value for each chart based on a plurality of factors; and
   present one or more of the plurality of charts based on corresponding score value for display, wherein the presenting further comprises:
      presenting a visual display comprising a plurality of nodes, wherein the nodes represent variables of the multivariate data set and line connections between nodes are displayed differently based upon a bivariate relationship between the nodes connected by each line connection;
      facilitating navigation from the visual display comprising the plurality of nodes to a visual display of a first chart associated with a first variable of the multivariate data set in response to selection of a node corresponding with the first variable; and
      facilitating further navigation from the visual display of the first chart to a plurality of additional charts representing different variables associated with the first variable;
   wherein at least one chart of the first chart and the additional charts comprises a plot of data represented by one of a line chart, a point chart, an area chart, a bar chart, and a pie chart.

2. The system of claim 1, wherein one of the plurality of factors comprises strength of association between components of each chart.

3. The system of claim 1, wherein one of the plurality of factors comprises suitability of each chart component and the variable mapped to that chart component.

4. The system of claim 1, wherein one of the plurality of factors comprises complexity of each chart.

5. The system of claim 1, wherein the data module is configured to present one or more of the plurality of charts by presenting a subset of the plurality of charts, the subset of charts having greater score values.

6. The system of claim 1, wherein the data module is configured to generate a plurality of charts by initially reducing a search space of potential chart candidates to be considered for presentation based on corresponding score value by analyzing metadata associated with the multivariate data set in combination with statistical analysis of the data to determine relationships between variables of the multivariate data set.

7. The system of claim 1, wherein each node of the visual display is connected with at least one other node, and a connection between two nodes indicates a bivariate relationship between variables of the multivariate data set associated with the two nodes.

8. A computer program product comprising:
a storage device comprising a non-transitory computer readable storage medium having computer readable program code embodied therewith, the computer readable program code configured to:
generate a plurality of charts that visually represent data from a multivariate data set, wherein the generating a plurality of charts includes initially reducing a search space of potential chart candidates to be considered for presentation based on a corresponding score value by analyzing metadata associated with the multivariate data set in combination with statistical analysis of the data to determine relationships between variables of the multivariate data set, the determination of relationships between variables of the multivariate data set including a bivariate analysis that determines strengths for combinations of pairs of variables and a random forest model analysis that determines relationships between more than two variables;
map variables within the multivariate data set to components of each chart;
calculate a score value for each chart based on a plurality of factors; and
present one or more of the plurality of charts based on corresponding score value for display, wherein the presenting further comprises:
presenting a visual display comprising a plurality of nodes, wherein the nodes represent variables of the multivariate data set and line connections between nodes are displayed differently based upon a bivariate relationship between the nodes connected by each line connection;
facilitating navigation from the visual display comprising the plurality of nodes to a visual display of a first chart associated with a first variable of the multivariate data set in response to selection of a node corresponding with the first variable; and
facilitating further navigation from the visual display of the first chart to a plurality of additional charts representing different variables associated with the first variable;
wherein at least one chart of the first chart and the additional charts comprises a plot of data represented by one of a line chart, a point chart, an area chart, a bar chart, and a pie chart.

9. The computer program product of claim 8, wherein one of the plurality of factors comprises strength of association between components of each chart.

10. The computer program product of claim 8, wherein one of the plurality of factors comprises suitability of each chart component and the variable mapped to that chart component.

11. The computer program product of claim 8, wherein one of the plurality of factors comprises complexity of each chart.

12. The computer program product of claim 8, wherein the computer readable program code is configured to present one or more of the plurality of charts by presenting a subset of the plurality of charts, the subset of charts having greater score values.

13. The computer program product of claim 8, wherein the computer readable program code is configured to generate a plurality of charts by initially reducing a search space of potential chart candidates to be considered for presentation based on corresponding score value by analyzing metadata associated with the multivariate data set in combination with statistical analysis of the data to determine relationships between variables of the multivariate data set.

14. The computer program product of claim 8, wherein each node of the visual display is connected with at least one other node, and a connection between two nodes indicates a bivariate relationship between variables of the multivariate data set associated with the two nodes.

15. A computer-implemented method comprising:
generating a plurality of charts that visually represent data from a multivariate data set, wherein the generating a plurality of charts includes initially reducing a search space of potential chart candidates to be considered for presentation based on a corresponding score value by analyzing metadata associated with the multivariate data set in combination with statistical analysis of the data to determine relationships between variables of the multivariate data set, the determination of relationships between variables of the multivariate data set including a bivariate analysis that determines strengths for combinations of pairs of variables and a random forest model analysis that determines relationships between more than two variables;
mapping variables within the multivariate data set to components of each chart;
calculating a score value for each chart based on a plurality of factors; and
presenting one or more of the plurality of charts based on corresponding score value for display, wherein the presenting further comprises:
presenting a visual display comprising a plurality of nodes, wherein the nodes represent variables of the multivariate data set and line connections between nodes are displayed differently based upon a bivariate relationship between the nodes connected by each line connection;
facilitating navigation from the visual display comprising the plurality of nodes to a visual display of a first chart associated with a first variable of the multivariate data set in response to selection of a node corresponding with the first variable; and
facilitating further navigation from the visual display of the first chart to a plurality of additional charts representing different variables associated with the first variable;
wherein at least one chart of the first chart and the additional charts comprises a plot of data represented by one of a line chart, a point chart, an area chart, a bar chart, and a pie chart.

* * * * *